United States Patent [19]

Rogers et al.

[11] Patent Number: 5,783,587
[45] Date of Patent: Jul. 21, 1998

[54] BENZOYL PIPERIDINES/PYRROLIDINES FOR ENHANCING SYNAPTIC RESPONSE

[75] Inventors: Gary A. Rogers; Lena Nilsson, both of Santa Barbara, Calif.

[73] Assignee: The Regents of the University of California, Oakland, Calif.

[21] Appl. No.: 822,027

[22] Filed: Mar. 21, 1997

Related U.S. Application Data

[62] Division of Ser. No. 458,967, Jun. 2, 1995, Pat. No. 5,650,409.

[51] Int. Cl.$^6$ .......... A61K 31/445; A61K 31/40; C07D 211/06; C07D 295/00
[52] U.S. Cl. .......... 514/330; 514/423; 546/226; 548/539
[58] Field of Search .......... 546/226; 514/330, 514/423; 548/539

[56] References Cited

U.S. PATENT DOCUMENTS 3,406,177  10/1968  Yoho .................... 260/294.7
3,463,855   8/1969  Yoho .................... 424/267

OTHER PUBLICATIONS

Shono et al. Drug Metab. Dispos. (1981), 9(5), 476–80), 1981.

*Primary Examiner*—Mukund J. Shah
*Assistant Examiner*—Bruck Kifle
*Attorney, Agent, or Firm*—Townsend and Townsend and Crew LLP

[57] ABSTRACT

Benzoyl piperidines and pyrrolidines and compounds of related structure are disclosed for use in enhancing synaptic responses mediated by AMPA receptors. The compounds are effective in the treatment of subjects suffering from impaired nervous or intellectual functioning due to deficiencies in the number or strength of excitatory synapses or in the number of AMPA receptors. The compounds can also be used for the treatment of non-impaired subjects for enhancing performance in sensory-motor and cognitive tasks which depend on brain networks utilizing AMPA receptors, for improving the performance of subjects with memory deficiencies, for treating depression, alcoholism and schizophrenia, and for improving memory encoding.

15 Claims, No Drawings

1

BENZOYL PIPERIDINES/PYRROLIDINES FOR ENHANCING SYNAPTIC RESPONSE

CROSS REFERENCE TO RELATED APPLICATION

This application is a division of application Ser. No. 08/458,967, filed Jun. 2, 1995, now U.S. Pat. No. 5,650,409, the full contents of which are incorporated herein by reference.

This invention relates to the prevention and treatment of cerebral insufficiency, including enhancement of receptor functioning in synapses in brain networks responsible for higher order behaviors.

BACKGROUND OF THE INVENTION

The release of glutamate at synapses at many sites in the mammalian forebrain stimulates two classes of postsynaptic receptors. These classes are usually referred to as AMPA/quisqualate and N-methyl-D-aspartic acid (NMDA) receptors. AMPA/quisqualate receptors mediate a voltage-independent fast excitatory post-synaptic current (the "fast epsc") whereas NMDA receptors generate a voltage-dependent, slow excitatory current. Studies carried out in slices of hippocampus or cortex indicate that the AMPA receptor-mediated fast epsc is by far the dominant component at most glutamatergic synapses under most circumstances.

AMPA receptors are not evenly distributed across the brain but instead are largely restricted to telencephalon and cerebellum. These receptors are found in high concentrations in the superficial layers of neocortex, in each of the major synaptic zones of hippocampus, and in the striatal complex, as reported by Monaghan et al., in *Brain Research* 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that enhance the functioning of the AMPA receptor could have significant benefits for intellectual performance. Such drugs should also facilitate memory encoding. Experimental studies, such as those reported by Arai and Lynch, *Brain Research*, 598:173–184 (1992), indicate that increasing the size of AMEPA receptor-mediated synaptic response(s) enhances the induction of long-term potentiation (LTP). LTP is a stable increase in the strength of synaptic contacts that follows repetitive physiological activity of a type known to occur in the brain during learning. Compounds that enhance the functioning of the AMPA form of glutamate receptors facilitate the induction of LTP and the acquisition of learned tasks as measured by a number of paradigms. Granger et al., *Synapse* 15:326–329 (1993); Staubli et al., *PNAS* 91:777–781 (1994); Arai et al., *Brain Res.* 638:343–346 (1994); Staubli et al., *PNAS* 91:11158–11162 (1994); Shors et al., *Neurosci. Let.* 186:153–156 (1995); and International Patent Application Publication No. WO 94/02475 (PCT/US93/06916) (Lynch and Rogers, Regents of the University of California).

There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49:1–6 (1992). A possible prototype for a compound that selectively facilitates the AMPA receptor has recently been disclosed by Ito et al., *J. Physiol.* 424:533–543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials. See, for example, Staubli et al., *Psychobiology* 18:377–381 (1990) and Xiao et al., *Hippocampus* 1:373–380 (1991). Aniracetam has also been found to have an extremely rapid onset and washout, and can be applied repeatedly with no apparent lasting effects; these are valuable traits for behaviorally-relevant drugs. Unfortunately, the peripheral administration of aniracetam is not likely to influence brain receptors. The drug works only at high concentrations (about 1.0 mM), and Guenzi and Zanetti, *J. Chromatogr.* 530:397–406 (1990) report that about 80% of the drug is converted to anisoyl-GABA following peripheral administration in humans. The metabolite, anisoyl-GABA, has been found to have no aniracetam-like effects.

A class of compounds that do not display the low potency and inherent instability characteristic of aniracetam has recently been disclosed. These compounds, termed "ampakines," are disclosed in International Patent Application Publication No. WO 94/02475 (PCT/US93/06916) (Lynch and Rogers, Regents of the University of California). The ampakines are chemically more stable than aniracetam, and show improved bioavailability as judged by experiments performed by Positron Emission Tomography (PET)—see, for example, Staubli et al., in *PNAS* 91: 11158–11162 (1994).

SUMMARY OF THE INVENTION

It has now been discovered that synaptic responses mediated by AMPA receptors are increased by administration of a novel class of benzamide compounds, bearing certain similarities to the ampakines but patentably distinct overall. The ability of the novel compounds of this invention to increase AMPA receptor-mediated responses makes the compounds useful in serving a variety of purposes, including facilitating the learning of behaviors dependent upon AMPA receptors, and use as therapeutic drugs in conditions in which AMPA receptors or synapses utilizing these receptors are reduced in numbers or efficiency.

These and other aspects and advantages of the invention will become apparent from the description that follows.

DETAILED DESCRIPTION OF THE INVENTION AND PREFERRED EMBODIMENTS

The compounds of the present invention are benzamides having the following formula:

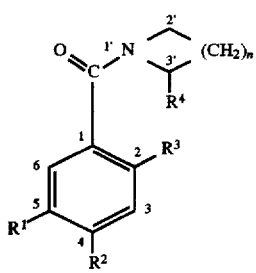

In this formula,

R[1] and R[2] are either the same or different and are each either H and $CH_2OR^5$, in which R[5] is either H, $C_1$–$C_6$ alkyl, an aromatic carbocyclic moiety, an aromatic heterocyclic moiety, an aromatic carbocyclic alkyl moiety, an aromatic heterocyclic alkyl moiety, or any such moiety substituted with one or more substituents selected from $C_1$–$C_3$ alkyl, $C_1$–$C_3$ alkoxy, hydroxy, halo, amino, alkylamino, dialkylamino (where alkyl is preferably $C_1$–$C_3$ alkyl), and methylenedioxy;

R[3] and R[4] are each H or together form either a single bond bridging the 2 and 3' ring vertices or a single divalent linking moiety linking the 2 and 3' ring vertices, the linking moiety being either —$CH_2$—, —$CH_2$—$CH_2$—, —CH=CH—, —O—, —N($R^6$)—, —N=C($R^6$)—, —C(O)—, —O—C(O)—, —C(O)—O—, —CH(OH)—, or —N($R^6$)—C(O)—, in which R[6] is H or $C_1$–$C_6$ alkyl; and n is 1, 2, 3 or 4.

In these definitions and in other portions of this specification and the appended claims where moieties linking the 2 and 3' ring vertices are designated, the left end of each moiety joins the no. 2 ring vertex and the right end joins the no. 3' ring vertex.

The term "aromatic carbocyclic moiety" is used herein to denote an aromatic ring or fused ring structure of carbon atoms with no hetero-atoms in the ring(s). Examples are phenyl, naphthyl, anthracyl, and phenanthracyl. Preferred examples are phenyl and naphthyl, with phenyl being the most preferred. The term "aromatic heterocyclic moiety" is used herein to denote an aromatic ring or fused ring structure of carbon atoms with one or more non-carbon atoms in the ring, or in one or more of the rings in fused ring structures. Examples are furyl, pyranyl, thienyl, pyrrolyl, pyridyl, pyrazolyl, pyrazinyl, pyrimidinyl, indolyl, quinolyl, isoquinolyl, quinoxalyl, and quinazolinyl. Preferred examples are furyl, pyranyl, pyrrolyl and pyridyl.

Within the class of compounds defined by the above formula, certain subclasses are preferred.

The group R[5], for example, is preferably either H, $C_1$–$C_6$ alkyl, substituted $C_1$–$C_6$ alkyl, phenyl, substituted phenyl, phenylalkyl, and substituted phenylalkyl, with the substituents being either $C_1$–$C_3$ alkyl, $C_1$–$C_3$ alkoxy, hydroxy, halo, amino, $C_1$–$C_3$ alkylamino, di($C_1$–$C_3$ alkyl)amino and methylenedioxy, or combinations of these substituents. More preferably, R[5] is either:

H;

$C_1$–$C_6$ alkyl;

$C_1$–$C_6$ alkyl substituted with hydroxy, halo, di($C_1$–C3 alkyl)amino or combinations of these substituents;

phenyl; or phenyl substituted with $C_1$–$C_3$ alkyl, $C_1$–$C_3$ alkoxy, hydroxy, halo, di($C_1$–$C_3$ alkyl)amino, methylenedioxy, or combinations of these substituents.

Still more preferably, R[5] is H, $C_1$–$C_3$ alkyl, phenyl or methylenedioxyphenyl.

R[1] and R[2] in preferred compounds are selected such that one of R[1] and R[2] is H and the other is $CH_2OR^5$.

Preferred divalent linking moieties to substitute for R[3] and R[4] are —$CH_2$—, —$CH_2$—$CH_2$—, —CH=CH—, —O—, —C(O)—, —O—C(O)—, —C(O)—O—, or —CH(OH)—. In still more preferred embodiments, R[3] and R[4] either are both H or together form a single oxygen atom (—O—) linking the no. 2 and no. 3' ring vertices.

Selected species within the scope of the formula are shown below for purposes of illustration.

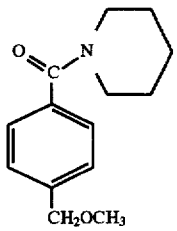

I

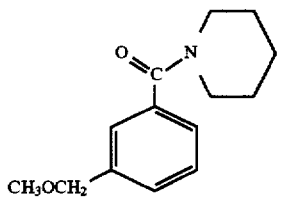

II

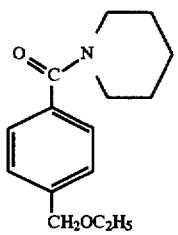

III

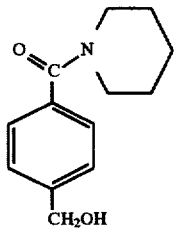

IV

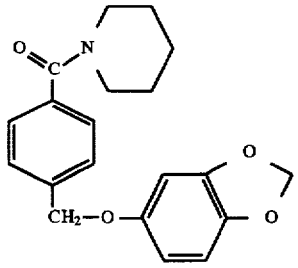

V

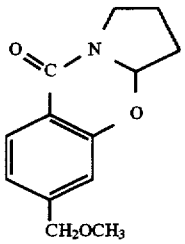

VI

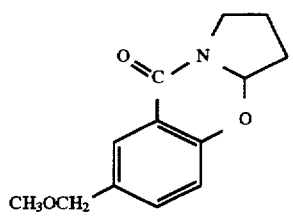

VII

The compounds of the present invention can be synthesized in a variety of ways, using conventional synthetic chemistry techniques. According to one reaction scheme, an α-halotoluic acid is contacted with at least two equivalents of an alkali salt of a lower alcohol according to the Williamson ether synthesis to produce an ether linkage. The resulting alkoxymethylbenzoic acid is activated with carbonyldiimidazole, thionyl chloride, dicyclohexylcarbodiimide, or any other suitable activating agent, and reacted with a suitable amine to achieve a carboxamide linkage.

In an alternate reaction scheme, a formyl-substituted aromatic carboxamide is prepared by activation of an appropriate starting acid with a tertiary amine (for example, triethyl amine) plus an acid chloride (for example, pivaloyl chloride) to produce a mixed anhydride for coupling to a suitable amine. The formyl group is then reduced to an alcohol by a suitable reducing agent such as sodium borohydride. The alcohol is then converted to a leaving group which is replaceable by the alkali salt of an alcohol. The leaving group can be generated by reagents such as thionyl chloride, thionyl bromide, mineral acids such as hydrochloric, hydrobromic or hydroiodic acids, or the combined action of a tertiary amine plus either a suitable sulfonic anhydride or sulfonyl halide. Alternatively, the alcohol can be activated by removing the proton. This is achieved by the action of a strong base such as sodium hydride in an aprotic solvent such as dimethylformamide. The resulting alkoxide is then reacted with a suitable alkyl halide or other alkyl compound with a suitable leaving group to produce the desired ether linkage.

Fused ring structures such as those in which $R^3$ and $R^4$ of the generic formula shown above are combined to form a single linking group bridging the 2 and 3' carbon atoms can be synthesized in the following manner. The carboxyl group of an appropriately substituted salicylic acid is activated with carbonyldiimidazole in dichloromethane, chloroform, tetrahydrofuran, or other anhydrous solvent. An aminoalkylacetal such as $H_2N(CH_2)_3CH(OCH_2CH_3)_2$ is then added. The resulting amide is treated with an aryl or alkyl sulfonic acid, trifluoroacetic acid, or other strong acid, in a solvent of low basicity such as chloroform or dichloromethane, to cleave the acetal and cyclize the intermediate aldehyde with the amide nitrogen and the phenolic oxygen.

The compounds of this invention can be incorporated into a variety of formulations for therapeutic administration. Examples are capsules, tablets, syrups, suppositories, and various injectable forms. Administration of the compounds can be achieved in various ways, including oral, bucal, rectal, parenteral, and intraperitoneal administration. Dose levels can vary widely, and optimal dosages for any particular patient or condition are readily determinable by those of skill in the art. Typical dosages can range from milligrams to decigrams. Preferred formulations of the compounds are oral preparations, particularly capsules or tablets containing each from about 1 milligram up to about 100 milligrams of active ingredient. Depending on the strength of the compound, a typical dosage may be one 10-mg tablet taken once a day, or one time-release capsule or tablet of 1-2 mg taken once a day. The time-release effect may be obtained by capsule materials that dissolve at different pH values, by capsules that release slowly by osmotic pressure, or by any other known means of controlled release. Subjects contemplated for treatment with the compounds of the invention include humans, domesticated animals, laboratory animals, and livestock.

The compounds of this invention are useful in a variety of ways. They can serve, for example, as a research tool for studying the biophysical and biochemical properties of the AMPA receptor and the consequences of selectively enhancing excitatory transmission on the operation of neuronal circuitry. Since the compounds reach central synapses, they will allow for testing of the behavioral effects of enhancing AMPA receptor currents.

As metabolically stable variants of aniracetam, the compounds of this invention have many potential applications in humans. For example, increasing the strength of excitatory synapses could compensate for losses of synapses or receptors associated with aging and brain disease (Alzheimer's disease, for example). Enhancing AMPA receptors could cause more rapid processing by multisynaptic circuitries found in higher brain regions and thus could produce an increase in perceptual-motor and intellectual performance. As another example, because increasing AMPA receptor-mediated responses facilitates synaptic changes of the type believed to encode memory, the compounds of this invention are expected to be functional as memory enhancers. Additional applications contemplated for the compounds of this invention include improving the performance of subjects with sensory-motor problems dependent upon brain networks utilizing AMPA receptors, improving the performance of subjects impaired in cognitive tasks dependent upon brain networks utilizing AMPA receptors, improving the performance of subjects with memory deficiencies, treating depression, alcoholism and schizophrenia, and improving the recovery of subjects suffering from trauma.

Accordingly, the compounds of this invention in suitable formulations can be employed for decreasing the amount of time needed to learn a cognitive, motor or perceptual task. Alternatively, these compounds can be employed for increasing the time for which cognitive, motor or perceptual tasks are retained. Still further, these compounds can be employed for decreasing the quantity and/or severity of errors made in recalling a cognitive, motor or perceptual task. Such treatment can prove especially advantageous in individuals who have suffered injury to the nervous system, or who have endured disease of the nervous system, especially injury or disease that affects the number of AMPA receptors in the nervous system.

The following examples are offered for purposes of illustration. The compounds addressed by these examples are those whose formulas are shown above, numbered by Roman numerals corresponding to those beneath the appropriate formulas.

EXAMPLE 1

Preparation of 1-(4'-Methoxymethylbenzoyl)
piperidine (Compound I; per generic formula:
$R^1=R^3=R^4=H, R^2=CH_2OCH_3$)

The synthesis of 1-(4'-methoxymethylbenzoyl)piperidine began with the preparation of 4-methoxymethylbenzoic acid from 4-bromomethylbenzoic acid by the Williamson ether synthesis. Specifically, 0.9 g (39 mmol) of sodium was added to 30 mL of methanol with cooling by water bath. After the sodium had reacted, 2.237 g (10.4 mmol) of the bromo acid was added and the solution was refluxed for 2 hours. Methanol was removed on a rotary evaporator after the addition of 5 mL of water, leaving a white residue. The residue was then dissolved in 50 mL of water and the solution was acidified to pH<2 with 6N HCl to yield a white precipitate. The product was partitioned between $CH_2Cl_2$ and water and the aqueous phase was washed three times with $CH_2Cl_2$. The $CH_2Cl_2$ washes were combined with the original $CH_2Cl_2$ phase and this solution was dried over $Na_2SO_4$. The drying agent was then removed by filtration and the solvent was removed on a rotary evaporator to yield 1.636 g of white 4-methoxymethylbenzoic acid with a melting point of 119.1°–119.6° C.

The 4-methoxymethylbenzoic acid was suspended with stirring in 20 mL $CH_2Cl_2$ to which was added 1.57 g carbonyldiimidazole (CDI). After 1 hour, 1.1 mL piperidine was added and after two additional hours the reaction mixture was diluted with diethyl ether and extracted with 1N HCl followed by 10% aqueous $NaHCO_3$. The solvent was removed on a rotary evaporator to yield 2.22 g of yellow oil. Bulb to bulb distillation at about 120° C. produced a colorless oil. Nuclear magnetic resonance spectroscopy (NMR) at 500 MHz revealed resonances at 7.37 (4H, AB quartet); 4.47 (2H, s); 3.72 (2H, br s); 3.41 (3H, s); 3.33 (2H, br s); 1.67 (4H, br s); and 1.5 ppm (2H, br s), relative to TMS, confirming the structure as that of 1-(4'-methoxymethylbenzoyl)piperidine.

EXAMPLE 2

Preparation of 1-(3'-Methoxymethylbenzoyl) piperidine (Compound II: $R^1$=$CH_2OCH_3$, $R^2$=$R^3$=$R^4$=H)

Commercially available 3-chloromethylbenzoyl chloride (1.00 g; 5.29 mmol) was added to 20 mL ice-cold methanol that contained a 5% molar excess of piperidine. After 5 minutes, 600 mg of NaH was added over a 4-minute period. The ice bath was removed and the solution was heated to reflux for about 15 minutes. The cooled solution was diluted with 70 mL water and the methanol was removed on a rotary evaporator. The aqueous solution was acidified with 5 mL of 6N HCl and extracted with three portions of $CH_2Cl_2$ and two portions of diethyl ether. The organic solutions were combined, extracted with 20 mL 10% aqueous $Na_2CO_3$, and dried over $Na_2SO_4$. The solvents were removed on a rotary evaporator to give a nearly colorless oil. Purification on silica gel to remove a small amount of methyl ester provided pure product. Infrared spectroscopy (IR): amide carbonyl at 1630 $cm^{-1}$. $^1$H NMR: δ7.37 (3H, m); 7.30 (1H, m); 4.47 (2H, s); 3.7 (2H, br s); 3.40 (3H, s); 3.35 (2H, br s); 1.67 (4H, br s); and 1.52 ppm (2H, br s). Collectively, these confirmed the structure of the product as that of 1-(3'-methoxymethylbenzoyl)piperidine.

EXAMPLE 3

Preparation of 1-(4'-Ethoxymethylbenzoyl) piperidine (Compound III: $R^1$=$R^3$=$R^4$=H, $R^2$=$CH_2OC_2H_5$)

A procedure identical to that described in Example 1 above was followed, except that ethanol was substituted for methanol. $^1$H NMR: δ7.37 (4H, s); 4.52 (2H, s); 3.7 (2H, br s); 3.56 (2H, q, J=6.87 Hz); 3.34 (2H, br s); 1.67 (4H, br s); 1.5 (2H, br s); and 1.26 ppm (3H, t, J=6.98 Hz). The structure of the product was thus confirmed as that of 1-(4'-ethoxymethylbenzoyl)piperidine.

EXAMPLE 4

Preparation of 1-(4'-Hydroxymethylbenzoyl) piperidine (Compound IV: $R^1$=$R^3$=$R^4$=H, $R^2$=$CH_2OH$)
and 1-(4'-(3",4"-Methylenedioxyphenoxy)-methylbenzoyl)piperidine (Compound V: $R^1$=$R^3$=$R^4$=H, $R^2$=3,4-methylenedioxyphenoxymethyl)

Synthesis of these compounds was begun by suspending 4-carboxybenzaldehyde (34.5 mmol) in 50 mL $CH_2Cl_2$, adding 5 mL triethylamine and, after 5 minutes, 4.25 mL pivaloyl chloride. After 1.5 hours, 3.42 mL piperidine was added to the stirred reaction and, after 2 hours, the solution was diluted with ether and washed two times with 5% $NaHCO_3$, three times with dilute HCl, and finally a saturated solution of NaCl. The organic solution was dried over $Na_2SO_4$ and the solvents were removed on a rotary evaporator to yield 7.38 g of 1-(4'-formylbenzoyl)piperidine.

The aldehyde (28.6 mmol) thus formed was dissolved in 40 mL of absolute ethanol, and 540 mg $NaBH_4$ was added over 2 hours. When thin-layer chromatography revealed no remaining aldehyde, the reaction was quenched with 2.5 mL acetic acid. The ethanol was removed on a rotary evaporator and the residue was taken up in 30 mL water. The product alcohol was extracted with two 25-mL volumes of $CH_2Cl_2$ plus 25 mL ether. The organic extracts were combined and dried over $Na_2SO_4$. Removal of the solvents on a rotary evaporator yielded 4.08 g of 1-(4'-hydroxymethylbenzoyl)piperidine, which was collected by filtration and washed with petroleum ether. The product (Compound IV, 1-(4'-hydroxymethylbenzoyl)piperidine) had a melting point of 119.6°–122.7° C. $^1$H NMR showed the methylene protons at 4.715 (2H, d, J=5.5 Hz) ppm.

The alcohol (6.97 mmol) of the preceding paragraph was dissolved in 15 mL $CHCl_3$, followed by the addition of 0.66 mL thionyl chloride. The solution was refluxed for 1 hour and then allowed to stand at room temperature overnight. The volume was then reduced by 50% on a rotary evaporator and the solution was diluted with $CCl_4$ and petroleum ether to induce crystallization. The product 1-(4'-chloromethylbenzoyl)piperidine was isolated in 92% yield and had a melting point of 106°–108° C.

Compound V was then synthesized by the Williamson ether method. To perform the synthesis, the anion of sesamol (3,4-methylenedioxyphenol) was generated in dry dimethylformamide by the action of NaH. The chloride from the preceding paragraph was added to the phenoxide, which produced the desired product in 84% yield with a melting point of 93.4°–93.7° C. The $^1$H NMR spectrum displayed resonances at 7.42 (4H, AB quartet); 6.70 (1H, d, J=8.45 Hz); 6.556 (1H, d, J=2.41 Hz); 6.39 (1H, q, J=2.41 and 8.51 Hz); 5.917 (2H, s); 5.007 (2H, s); 3.7 (2H, br s); 3.35 (2H, br s); 1.7 (4H, br s), and 1.5 ppm (2H, br s), confirming the structure as that of 1-(4'-(3",4"-methylenedioxyphenoxy)methylbenzoyl)piperidine (Compound V).

EXAMPLE 5

Preparation of (R, S)-6-Methoxymethyl-2,3-dihydro-1H-pyrrolo[2,1-b][1,3]benzoxazine-9(3aH)-one (Compound VI: $R^1$=H, $R^2$=$CH_2OCH_3$, {$R^3$+$R^4$}=—O—)

(The ring vertex numbering system used in the nomenclature of this compound differs from that of the generic formula because of the fused ring structure formed by the joinder of $R^3$ and $R^4$.)

The bromination of 4-methylsalicylic acid was performed in $CCl_4$ using $Br_2$ under illumination by a 500W quartz/halogen lamp. The resulting 4-bromomethylsalicylic acid was converted to 4-methoxymethylsalicylic acid by the Williamson ether synthesis in methanol containing four equivalents of methoxide.

4-Methoxymethylsalicylic acid (1.72 g; containing some 4-methylsalicylic acid) was treated with 1.65 g carbonyidiimidazole in 15 mL ether and 20 mL $CH_2Cl_2$. After the reaction was complete (about 30 minutes), 2.0 mL 4-aminobutyraldehyde diethyl acetal was added with stirring. Most of the solvents were removed on a rotary evaporator after 2 hours and the concentrated solution was diluted with ether. The organic solution was washed with dilute HCl, two times with 5% $NaHCO_3$, two times with dilute HCl, and finally with saturated NaCl. The solution was dried over $Na_2SO_4$ and the solvents were removed on a rotary evaporator to yield a pale yellow oil corresponding to the amide acetal. The oil was dissolved in 10 mL $CHCl_3$ to which was added 100 mg (+)-camphorsulfonic acid. The solution was allowed to stand at room temperature overnight. Removal of the solvent and chromatographic purification on silica gel gave pure product. IR spectrum: amide carbonyl stretching mode at 1670 cm$^{-1}$. $^1$H NMR: resonances at 7.90 (1H, d, J=7.87 Hz); 7.06 (1H, d, J=8.07 Hz); 6.956 (1H, s); 5.487 (1H, t, J=5.84 Hz); 4.457 (2H, s); 3.845 (1H, dt, J=11.48 and 7.25 Hz); 3.59–3.64 (1H, ddd, J=11.53, 8.01, and 5.11 Hz); 3.401 (3H, s); 2.40–2.47 (1H, m); 2.22–2.29 (1H, m); 2.07–2.15 (1H, m); and 1.89–1.98 ppm (1H, m), confirming the structure as that of (R,S)-6-methoxymethyl-2,3-dihydro-1H-pyrrolo[2,1-b][1,3]benzoxazine-9(3aH)-one.

EXAMPLE 6

Preparation of (R,S)-7-Methoxymethyl-2,3-dihydro-1H-pyrrolo[2, 1-b][1,3]benzoxazine-9(3aH)-one (Compound VII: $R^1$=$CH_2OCH_3$, $R^2$=$R^5$=H, $\{R^3+R^4\}$=—O—)

This compound was synthesized by the procedures outlined above starting with 5-formylsalicylic acid to yield a white solid with the following $^1$H NMR resonances: 7.88 (1H, d, J=2.04 Hz); 7.43 (1H, q, J=8.36 and 2.10 Hz); 6.956 (1H, d, J=8.36 Hz); 3.60–3.64 (1H, m); 3.37 (3H, s); 2.40–2.47 (1H, m); 2.22–2.29 (1H, m); 2.08–2.16 (1H, m); and 1.90–1.99 ppm (1H, m), confirming the structure as that of (R,S)-7-methoxymethyl-2,3-dihydro-1H-pyrrolo[2,1-b][1,3]benzoxazine-9(3aH)-one.

EXAMPLE 7

In Vitro Physiological Testing

The physiological effects of the compounds of this invention were determined by in vitro tests using slices of rat hippocampus according to the following procedure. Excitatory responses (field EPSPs) were measured in hippocampal slices, which are maintained in a recording chamber continuously perfused with artificial cerebrospinal fluid (ACSF). During a 15-minute interval, the perfusion medium was switched to one containing various concentrations of the test compounds. Responses collected immediately before and at the end of drug perfusion were superimposed in order to calculate both the percent increase in EPSP amplitude and the percent increase in the width of the response at one-half the peak height (half-width).

To conduct these tests, the hippocampus was removed from anesthetized, 2-month old Sprague-Dawley rats, and in vitro slices (400 micrometers thick) were prepared and maintained in an interface chamber at 35° C. using conventional techniques. This is the procedure used by Dunwiddie and Lynch, as reported in *J. Physiol.* 276:353–367 (1978). The chamber was constantly perfused at 0.5 mL/min with ACSF containing (in mM): NaCl, 124; KCl, 3; $KH_2PO_4$, 1.25; $MgSO_4$, 2.5; $CaCl_2$, 3.4; $NaHCO_3$, 26; glucose, 10; and L-ascorbate, 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activated a population of the Schaffer-commissural (SC) fibers, which arise from neurons in the subdivision CA3 and terminate in synapses on the dendrites of CA1 neurons. Activation of these synapses causes them to release the transmitter glutamate. Glutamate binds to the postsynaptic AMPA receptors, which then transiently open an associated ion channel and permit a sodium current to enter the postsynaptic cell. This current results in a voltage in the extracellular space (the field excitatory post-synaptic potential or field "EPSP"), which is recorded by a high impedance recording electrode positioned in the middle of the stratum radiatum of CA1.

With the intensity of the stimulation current adjusted to produce half-maximal EPSPs (typically about 1.5–2.0 mV), paired stimulation pulses were given every 40 seconds with an interpulse interval of 200 msec. The field EPSPs of the second response were digitized and analyzed to determine amplitude and half-width. If the responses are stable for 15–30 minutes (baseline), test compounds were added to the perfusion lines for a period of about 15 minutes. The perfusion was then changed back to regular ACSF.

Paired-pulse stimulation is used in this type of test because stimulation of the SC fibers in part activates interneurons that generate an inhibitory postsynaptic potential (IPSP) in the pyramidal cells of CA1. This feed-forward IPSP typically sets in after the EPSP reaches its peak. The feed-forward IPSP accelerates the repolarization and shortens the decay phase of the EPSP, and could thereby partially mask the effects of the test compounds. One of the relevant features of the feed-forward IPSP is that it cannot be reactivated for several hundred milliseconds following a stimulation pulse. This phenomenon can be employed to advantage to eliminate IPSP by delivering paired pulses separated by 200 milliseconds and using the second ("primed") response for data analysis.

The field EPSP recorded in field CA1 after stimulation of CA3 axons is known to be mediated by AMPA receptors: the receptors are present in the synapses, as reported by Kessler, et al., *Brain Res.* 560:337–341 (1991), and drugs that selectively block the receptor selectively block the field EPSP. Aniracetam increases the mean open time of the AMPA receptor channel and thus increases the amplitude of the synaptic current and prolongs its duration. These effects are mirrored in the field EPSP, as reported in the literature. See, for example, Staubli, et al., *Psychobiology* 18:377–381 (1990); Xiao, et al., *Hippocampus* 1:373–380 (1991); and Staubli, et al., *Hippocampus* 2:49–58 (1992). Aniracetam and ampakines augment the amplitude of the response and extend the duration of the response.

The table below lists estimates of the concentration of each test compound that would be required to increase the amplitude of the EPSP to a value 25% above the baseline level (ACSF fluid only). Also listed in the table are estimates of the concentrations of each test compound that would be required to increase the half-width of the EPSP by 50%. These parameters were chosen as markers of robust results that represent about a quarter of the respective maximal effects seen with a large number of ampakines. The data in the table indicates that the compounds produced dose-dependent increases in both measures, and were effective at concentrations as low as 50 µM.

TABLE

Compounds and Test Data

| Compound | $R^1$ | $R^2$ | $R^3$ | $R^4$ | n | +25% Amplitude (mM) | +50% Half-Width (mM) |
|---|---|---|---|---|---|---|---|
| I | H | $CH_2OCH_3$ | H | H | 3 | 0.3 | 0.3 |
| II | $CH_2OCH_3$ | H | H | H | 3 | 0.3 | >1 |
| III | H | $CH_2OC_2H_5$ | H | H | 3 | >1 | 0.2 |
| IV | H | $CH_2OH$ | H | H | 3 | 1 | >1 |
| V | H | 3,4-methylenedioxy-phenoxymethyl | H | H | 3 | 0.05 | >0.1 |
| VI | H | $CH_2OCH_3$ | —O— | | 2 | 0.1 | 0.2 |
| VII | $CH_2OCH_3$ | H | —O— | | 2 | 0.3 | 0.2 |

The foregoing is offered primarily for purposes of illustration. It will be readily apparent to those skilled in the art that the dosages, methods of administration, and other parameters of the invention described herein may be further modified or substituted in various ways without departing from the spirit and scope of the invention.

We claim:

1. A compound having the formula, with ring vertices numbered as shown:

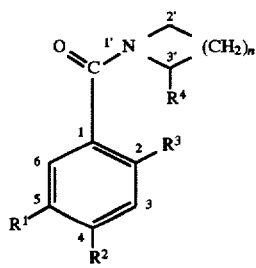

in which:
one of $R^1$ and $R^2$ is H and the other is $CH_2OR^5$, in which $R^5$ is a member selected from the group consisting of $C_1$–$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$–$C_3$ alkyl, $C_1$–$C_3$ alkoxy, hydroxy, halo, amino, alkylamino, dialkylamino, and methylenedioxy;

$R^3$ and $R^4$ are each H; and n is 2 or 3.

2. A compound in accordance with claim 1 in which $R^5$ is a member selected from the group consisting of $C_1$–$C_6$ alkyl, substituted $C_1$–$C_6$ alkyl, phenyl, substituted phenyl, phenylalkyl, and substituted phenylalkyl, with substituents selected from the group consisting of $C_1$–$C_3$ alkyl, $C_1$–$C_3$ alkoxy, hydroxy, halo, dialkylamino, and methylenedioxy.

3. A compound in accordance with claim 1 in which $R^5$ is a member selected from the group consisting of:

$C_1$–$C_6$ alkyl;

$C_1$–$C_6$ alkyl substituted with a member selected from the group consisting of hydroxy, halo and dialkylamino;

phenyl; and phenyl substituted with a member selected from the group consisting of $C_1$–$C_3$ alkyl, $C_1$–$C_3$ alkoxy, hydroxy, halo, amino, and methylenedioxy.

4. A compound in accordance with claim 1 in which $R^5$ is a member selected from the group consisting of $C_1$–$C_3$ alkyl, phenyl and methylenedioxyphenyl.

5. A compound in accordance with claim 1 in which $R^1$ is H, $R^2$ is methoxymethyl, $R^3$ is H, $R^4$ is H, and n is 3.

6. A compound in accordance with claim 1 in which $R^1$ is methoxymethyl, $R^2$ is H, $R^3$ is H, $R^4$ is H, and n is 3.

7. A compound in accordance with claim 1 in which $R^1$ is H, $R^2$ is ethoxymethyl, $R^3$ is H, $R^4$ is H, and n is 3.

8. A compound in accordance with claim 1 in which $R^1$ is H, $R^2$ is 3,4-methylenedioxyphenoxymethyl, $R^3$ is H, $R^4$ is H, and n is 3.

9. A method for the treatment of a subject to enhance synaptic response mediated by AMPA receptors, said method comprising administering to said subject an effective amount of a compound having the formula, with ring vertices numbered as shown:

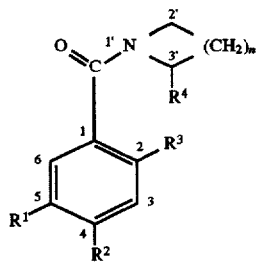

in which:
one of $R^1$ and $R^2$ is H and the other is $CH_2OR^5$, in which $R^5$ is a member selected from the group consisting of H, $C_1$–$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$–$C_3$ alkyl, $C_1$–$C_3$ alkoxy, hydroxy, halo, amino, alkylamino, dialkylamino, and methylenedioxy;

$R^3$ and $R^4$ are each H or together form either a single bond bridging the 2 and 3' ring vertices or a single divalent linking moiety linking the 2 and 3' ring vertices, the linking moiety being either —$CH_2$—, —$CH_2$—$CH_2$—, —CH=CH—, —$N(R^6)$—, —$N=C(R^6)$—, —C(O)—, —C(O)—, —C(O)—O—, —CH(OH)—, or —$N(R^6)$—C(O)—, in which $R^6$ is H or $C_1$-$C_6$ alkyl; and n is 2 or 3.

10. A method in accordance with claim 9 in which $R^5$ is a member selected from the group consisting of $C_1$-$C_3$ alkyl, phenyl and methylenedioxyphenyl.

11. A method in accordance with claim 9 in which $R^1$ is H, $R^2$ is methoxymethyl and n is 3.

12. A method in accordance with claim 9 in which $R^1$ is methoxymethyl, $R^2$ is H and n is 3.

13. A method in accordance with claim 9 in which $R^1$ is H, $R^2$ is ethoxymethyl and n is 3.

14. A method in accordance with claim 9 in which $R^1$ is H, $R^2$ is hydroxymethyl and n is 3.

15. A method in accordance with claim 9 in which $R^1$ is H, $R^2$ is 3,4-methylenedioxyphenoxymethyl and n is 3.

* * * * *